(12) United States Patent
Huebner (10) Patent No.: US 7,189,237 B2
(45) Date of Patent: Mar. 13, 2007

(54) DEFORMABLE BONE PLATES

(75) Inventor: Randall J. Huebner, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 449 days.

(21) Appl. No.: 10/717,402

(22) Filed: Nov. 19, 2003

(65) Prior Publication Data

US 2004/0102777 A1  May 27, 2004

Related U.S. Application Data

(60) Provisional application No. 60/512,136, filed on Oct. 17, 2003, provisional application No. 60/427,908, filed on Nov. 19, 2002.

(51) Int. Cl.
*A61B 17/56* (2006.01)
*A61F 2/30* (2006.01)

(52) U.S. Cl. ...................................... 606/69
(58) Field of Classification Search .............. 606/69, 606/70, 71–73
See application file for complete search history.

(56) References Cited

U.S. PATENT DOCUMENTS

| | | | |
|---|---|---|---|
| 820,503 A | 5/1906 | Krengel et al. |
| 869,697 A | 10/1907 | Eilhauer et al. |
| 1,105,105 A | 7/1914 | Sherman |
| 1,345,425 A | 7/1920 | Wells |
| 1,789,060 A | 1/1931 | Weisenbach |
| 1,889,239 A | 11/1932 | Crowley |
| 2,406,832 A | 9/1946 | Hardinge |
| 2,443,363 A | 6/1948 | Townsend et al. |
| 2,489,870 A | 11/1949 | Dzus |
| 2,494,229 A | 1/1950 | Collison |
| 2,500,370 A | 3/1950 | McKibbin |
| 2,526,959 A | 10/1950 | Lorenzo |
| 2,580,821 A | 1/1952 | Nicola |
| 2,583,896 A | 1/1952 | Siebrandt |
| 2,737,835 A | 3/1956 | Herz |
| 3,025,853 A | 3/1962 | Mason |
| 3,072,423 A | 1/1963 | Charlton |
| 3,171,518 A | 3/1965 | Bergmann |
| 3,244,170 A | 4/1966 | McElvenny |
| 3,346,894 A | 10/1967 | Lemelson |
| 3,386,437 A | 6/1968 | Treace |
| 3,488,779 A | 1/1970 | Christensen |
| 3,489,143 A | 1/1970 | Halloran |
| 3,593,709 A | 7/1971 | Halloran |

(Continued)

FOREIGN PATENT DOCUMENTS

AU  89750/91  2/1992

(Continued)

OTHER PUBLICATIONS

McBride S.M.O. Stainless Steel Bone Plates brochure, DePuy, Inc., 1943.

(Continued)

*Primary Examiner*—Anu Ramana
(74) *Attorney, Agent, or Firm*—Kolisch Hartwell, P.C.

(57) ABSTRACT

Bone plates configured to be deformed after the bone plates have being secured to bone, apparatus including the bone plates, and methods of using the bone plates to fix bones.

18 Claims, 4 Drawing Sheets

U.S. PATENT DOCUMENTS

| | | |
|---|---|---|
| 3,604,414 A | 9/1971 | Borges |
| 3,716,050 A | 2/1973 | Johnston |
| 3,741,205 A | 6/1973 | Markolf et al. |
| 3,842,825 A | 10/1974 | Wagner |
| 3,866,458 A | 2/1975 | Wagner |
| 3,900,025 A | 8/1975 | Barnes, Jr. |
| 3,901,064 A | 8/1975 | Jacobson |
| 3,939,497 A | 2/1976 | Heimke et al. |
| 3,965,720 A | 6/1976 | Goodwin et al. |
| 4,119,092 A | 10/1978 | Gil |
| 4,187,840 A | 2/1980 | Watanabe |
| 4,187,841 A | 2/1980 | Knutson |
| 4,201,215 A | 5/1980 | Crossett et al. |
| 4,364,382 A | 12/1982 | Mennen |
| 4,388,921 A | 6/1983 | Sutter et al. |
| 4,408,601 A | 10/1983 | Wenk |
| 4,414,967 A * | 11/1983 | Shapiro ................. 606/75 |
| RE31,628 E | 7/1984 | Allgower et al. |
| 4,457,307 A | 7/1984 | Stillwell |
| 4,484,570 A | 11/1984 | Sutter et al. |
| 4,493,317 A | 1/1985 | Klaue |
| 4,506,681 A | 3/1985 | Mundell |
| 4,513,744 A | 4/1985 | Klaue |
| 4,565,192 A | 1/1986 | Shapiro |
| 4,565,193 A | 1/1986 | Streli |
| 4,573,458 A | 3/1986 | Lower |
| 4,651,724 A | 3/1987 | Berentey et al. |
| 4,683,878 A | 8/1987 | Carter |
| 4,703,751 A | 11/1987 | Pohl |
| 4,718,413 A | 1/1988 | Johnson |
| 4,730,608 A | 3/1988 | Schlein |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,794,918 A | 1/1989 | Wolter |
| 4,800,874 A | 1/1989 | David et al. |
| 4,823,780 A | 4/1989 | Odensten et al. |
| 4,867,144 A | 9/1989 | Karas et al. |
| 4,892,093 A | 1/1990 | Zarnowski et al. |
| 4,893,619 A | 1/1990 | Dale et al. |
| 4,903,691 A | 2/1990 | Heinl |
| 4,905,679 A | 3/1990 | Morgan |
| 4,923,471 A | 5/1990 | Morgan |
| 4,926,847 A | 5/1990 | Luckman |
| 4,943,292 A | 7/1990 | Foux |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karas et al. |
| 4,966,599 A | 10/1990 | Pollock |
| 4,973,332 A | 11/1990 | Kummer |
| 4,988,350 A | 1/1991 | Herzberg |
| 5,002,544 A | 3/1991 | Klaue et al. |
| 5,006,120 A | 4/1991 | Carter |
| 5,013,315 A | 5/1991 | Barrows |
| 5,015,248 A | 5/1991 | Burstein et al. |
| 5,021,056 A | 6/1991 | Hofmann et al. |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,129,899 A | 7/1992 | Small et al. |
| 5,133,718 A | 7/1992 | Mao |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |
| 5,190,544 A | 3/1993 | Chapman et al. |
| 5,190,545 A | 3/1993 | Corsi et al. |
| 5,197,966 A | 3/1993 | Sommerkamp |
| 5,201,737 A | 4/1993 | Leibinger et al. |
| 5,234,431 A | 8/1993 | Keller |
| 5,254,119 A | 10/1993 | Schreiber |
| 5,269,784 A | 12/1993 | Mast |
| 5,290,288 A | 3/1994 | Vignaud et al. |
| 5,304,180 A | 4/1994 | Slocum |
| 5,314,490 A | 5/1994 | Wagner et al. |
| 5,364,398 A | 11/1994 | Chapman et al. |
| 5,364,399 A | 11/1994 | Lowery et al. |
| 5,380,327 A | 1/1995 | Eggers et al. |
| 5,413,577 A | 5/1995 | Pollock |
| 5,413,579 A | 5/1995 | Du Toit |
| 5,423,826 A | 6/1995 | Coates et al. |
| 5,443,516 A | 8/1995 | Albrektsson et al. |
| 5,468,242 A | 11/1995 | Reisberg |
| 5,474,553 A | 12/1995 | Baumgart |
| 5,487,741 A | 1/1996 | Maruyama et al. |
| 5,487,743 A | 1/1996 | Laurain et al. |
| 5,522,902 A | 6/1996 | Yuan et al. |
| 5,527,311 A | 6/1996 | Proctor et al. |
| 5,531,745 A | 7/1996 | Ray |
| 5,534,027 A | 7/1996 | Hodorek |
| 5,545,228 A | 8/1996 | Kambin |
| 5,564,302 A | 10/1996 | Watrous |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,607,426 A | 3/1997 | Ralph et al. |
| 5,643,261 A | 7/1997 | Schafer et al. |
| 5,643,265 A | 7/1997 | Errico et al. |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,667 A | 10/1997 | Hausman |
| 5,681,313 A | 10/1997 | Diez |
| 5,700,267 A * | 12/1997 | Urbanski ................. 606/86 |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,807,396 A | 9/1998 | Raveh |
| 5,810,823 A | 9/1998 | Klaue et al. |
| 5,810,824 A | 9/1998 | Chan |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,902,304 A | 5/1999 | Walker et al. |

| | | | | | |
|---|---|---|---|---|---|
| 5,904,683 A | 5/1999 | Pohndorf et al. | 6,454,769 B2 | 9/2002 | Wagner et al. |
| 5,916,216 A | 6/1999 | DeSatnick et al. | 6,454,770 B1 | 9/2002 | Klaue |
| 5,919,195 A | 7/1999 | Wilson et al. | 6,458,133 B1 | 10/2002 | Lin |
| 5,928,234 A | 7/1999 | Manspeizer | 6,503,250 B2 | 1/2003 | Paul |
| 5,931,839 A * | 8/1999 | Medoff .................. 606/69 | 6,508,819 B1 | 1/2003 | Orbay |
| 5,938,664 A | 8/1999 | Winquist et al. | 6,514,274 B1 | 2/2003 | Boucher et al. |
| 5,941,878 A | 8/1999 | Medoff | 6,520,965 B2 | 2/2003 | Chervitz et al. |
| 5,951,557 A | 9/1999 | Luter | 6,527,775 B1 | 3/2003 | Warburton |
| 5,954,722 A | 9/1999 | Bono | 6,533,789 B1 | 3/2003 | Hall, IV et al. |
| 5,964,763 A | 10/1999 | Incavo et al. | 6,547,790 B2 | 4/2003 | Harkey et al. |
| 5,968,046 A | 10/1999 | Castleman | 6,565,570 B2 | 5/2003 | Sterett et al. |
| 5,968,047 A | 10/1999 | Reed | 6,592,578 B2 | 7/2003 | Henniges et al. |
| 5,973,223 A | 10/1999 | Tellman et al. | 6,595,993 B2 | 7/2003 | Donno et al. |
| 6,001,099 A | 12/1999 | Huebner | 6,602,255 B1 | 8/2003 | Campbell et al. |
| 6,004,323 A | 12/1999 | Park et al. | 6,623,486 B1 | 9/2003 | Weaver et al. |
| 6,004,353 A | 12/1999 | Masini | 6,623,487 B1 | 9/2003 | Goshert |
| 6,007,535 A | 12/1999 | Rayhack et al. | 6,682,531 B2 | 1/2004 | Winquist et al. |
| 6,022,350 A | 2/2000 | Ganem | 6,682,533 B1 | 1/2004 | Dinsdale et al. |
| 6,027,504 A | 2/2000 | McGuire | 6,689,139 B2 | 2/2004 | Horn |
| 6,053,915 A | 4/2000 | Bruchmann | 6,695,846 B2 | 2/2004 | Richelsoph et al. |
| 6,077,266 A | 6/2000 | Medoff | 6,706,046 B2 | 3/2004 | Orbay et al. |
| 6,077,271 A | 6/2000 | Huebner et al. | 6,712,820 B2 | 3/2004 | Orbay |
| 6,093,188 A | 7/2000 | Murray | 6,719,759 B2 | 4/2004 | Wagner et al. |
| 6,096,040 A | 8/2000 | Esser | 6,730,090 B2 | 5/2004 | Orbay et al. |
| 6,113,603 A | 9/2000 | Medoff | 6,730,091 B1 | 5/2004 | Pfefferle et al. |
| 6,117,160 A | 9/2000 | Bonutti | 6,736,819 B2 | 5/2004 | Tipirneni |
| 6,123,709 A | 9/2000 | Jones | 6,767,351 B2 | 7/2004 | Orbay et al. |
| 6,129,728 A | 10/2000 | Schumacher et al. | 6,793,658 B2 | 9/2004 | LeHuec et al. |
| 6,129,730 A | 10/2000 | Bono et al. | 6,821,278 B2 | 11/2004 | Frigg et al. |
| 6,139,548 A | 10/2000 | Errico | 6,858,031 B2 | 2/2005 | Morrison et al. |
| 6,152,927 A | 11/2000 | Farris et al. | 6,866,665 B2 | 3/2005 | Orbay |
| 6,159,213 A | 12/2000 | Rogozinski | 6,893,444 B2 | 5/2005 | Orbay |
| 6,179,839 B1 | 1/2001 | Weiss et al. | 6,955,677 B2 | 10/2005 | Dahners |
| 6,183,475 B1 | 2/2001 | Lester et al. | 2001/0011172 A1 | 8/2001 | Orbay et al. |
| 6,193,721 B1 | 2/2001 | Michelson | 2002/0004660 A1 | 1/2002 | Henniges et al. |
| 6,197,028 B1 | 3/2001 | Ray et al. | 2002/0032446 A1 | 3/2002 | Orbay |
| 6,221,073 B1 | 4/2001 | Weiss et al. | 2002/0055741 A1 | 5/2002 | Schlapfer et al. |
| 6,224,602 B1 | 5/2001 | Hayes | 2002/0128654 A1 | 9/2002 | Steger et al. |
| 6,228,087 B1 | 5/2001 | Fenaroli et al. | 2002/0143336 A1 | 10/2002 | Hearn |
| 6,235,033 B1 | 5/2001 | Brace et al. | 2002/0143338 A1 | 10/2002 | Orbay et al. |
| 6,235,034 B1 | 5/2001 | Bray | 2002/0147453 A1 | 10/2002 | Gambale |
| 6,238,396 B1 | 5/2001 | Lombardo | 2002/0151899 A1 | 10/2002 | Bailey et al. |
| 6,258,092 B1 | 7/2001 | Dall | 2002/0156474 A1 | 10/2002 | Wack et al. |
| 6,261,291 B1 | 7/2001 | Talaber et al. | 2002/0183752 A1 | 12/2002 | Steiner et al. |
| 6,273,889 B1 | 8/2001 | Richelsoph | 2003/0040748 A1 | 2/2003 | Aikins et al. |
| 6,283,969 B1 | 9/2001 | Grusin et al. | 2003/0055429 A1 | 3/2003 | Ip et al. |
| 6,290,703 B1 | 9/2001 | Ganem | 2003/0105461 A1 | 6/2003 | Putnam |
| 6,302,883 B1 | 10/2001 | Bono | 2003/0149434 A1 | 8/2003 | Paul |
| 6,302,884 B1 | 10/2001 | Wellisz et al. | 2003/0153918 A1 | 8/2003 | Putnam et al. |
| 6,302,887 B1 | 10/2001 | Spranza et al. | 2003/0233093 A1 | 12/2003 | Moles et al. |
| 6,306,136 B1 | 10/2001 | Baccelli | 2004/0102775 A1 | 5/2004 | Huebner |
| 6,312,431 B1 | 11/2001 | Asfora | 2004/0102776 A1 | 5/2004 | Huebner |
| 6,315,779 B1 | 11/2001 | Morrison et al. | 2004/0102778 A1 | 5/2004 | Huebner et al. |
| 6,322,562 B1 | 11/2001 | Wolter | 2004/0116930 A1 | 6/2004 | O'Driscoll et al. |
| 6,325,803 B1 | 12/2001 | Schumacher et al. | 2004/0127901 A1 | 7/2004 | Huebner et al. |
| 6,331,179 B1 | 12/2001 | Freid et al. | 2004/0127903 A1 | 7/2004 | Schlapfer et al. |
| 6,336,927 B2 | 1/2002 | Rogozinski | 2004/0153073 A1 | 8/2004 | Orbay |
| 6,338,734 B1 | 1/2002 | Burke et al. | 2004/0193164 A1 | 9/2004 | Orbay |
| 6,342,055 B1 | 1/2002 | Eisermann et al. | 2004/0193165 A1 | 9/2004 | Orbay |
| 6,342,075 B1 | 1/2002 | MacArthur | 2004/0220566 A1 | 11/2004 | Bray |
| 6,355,036 B1 | 3/2002 | Nakajima | 2004/0260291 A1 | 12/2004 | Jensen |
| 6,355,042 B2 | 3/2002 | Winquist | 2004/0260292 A1 | 12/2004 | Orbay et al. |
| 6,358,250 B1 | 3/2002 | Orbay | 2004/0260293 A1 | 12/2004 | Orbay et al. |
| 6,364,881 B1 | 4/2002 | Apgar et al. | 2004/0260294 A1 | 12/2004 | Orbay et al. |
| 6,364,882 B1 | 4/2002 | Orbay | 2004/0260295 A1 | 12/2004 | Orbay et al. |
| 6,364,883 B1 | 4/2002 | Santilli | 2005/0015089 A1 | 1/2005 | Young et al. |
| 6,379,354 B1 | 4/2002 | Rogozinski | 2005/0049593 A1 | 3/2005 | Duong et al. |
| 6,379,364 B1 | 4/2002 | Brace et al. | 2005/0065520 A1 | 3/2005 | Orbay |
| 6,402,756 B1 | 6/2002 | Ralph et al. | 2005/0065522 A1 | 3/2005 | Orbay |
| 6,413,259 B1 | 7/2002 | Lyons et al. | 2005/0065523 A1 | 3/2005 | Orbay |
| 6,428,542 B1 | 8/2002 | Michelson | 2005/0065524 A1 | 3/2005 | Orbay |
| 6,436,103 B1 | 8/2002 | Suddaby | 2005/0065528 A1 | 3/2005 | Orbay |
| 6,440,135 B2 | 8/2002 | Orbay et al. | 2005/0085818 A1 | 4/2005 | Huebner |

| | | | |
|---|---|---|---|
| 2005/0085819 | A1 | 4/2005 | Ellis et al. |
| 2005/0131413 | A1 | 6/2005 | O'Driscoll et al. |
| 2005/0159747 | A1 | 7/2005 | Orbay |
| 2005/0165395 | A1 | 7/2005 | Orbay et al. |
| 2005/0165400 | A1 | 7/2005 | Fernandez |
| 2005/0171544 | A1 | 8/2005 | Falkner |
| 2005/0182405 | A1 | 8/2005 | Orbay et al. |
| 2005/0182406 | A1 | 8/2005 | Orbay et al. |
| 2005/0187551 | A1 | 8/2005 | Orbay et al. |
| 2005/0192578 | A1 | 9/2005 | Horst |
| 2005/0234458 | A1 | 10/2005 | Huebner |

FOREIGN PATENT DOCUMENTS

| | | |
|---|---|---|
| CH | 611 147 | 5/1979 |
| DE | 2515430 | 11/1975 |
| DE | 4201531 | 7/1993 |
| DE | 4343117 | 6/1995 |
| EP | 0 053 999 | 6/1982 |
| EP | 0 410 309 | 1/1991 |
| EP | 0415837 A2 | 3/1991 |
| EP | 0471418 A1 | 2/1992 |
| EP | 0362049 B1 | 5/1992 |
| EP | 1 250 892 A2 | 9/2003 |
| EP | 1 250 892 A3 | 9/2003 |
| FR | 742.618 | 3/1933 |
| FR | 2 254 298 | 7/1975 |
| FR | 2367479 | 5/1978 |
| FR | 2405705 | 5/1979 |
| FR | 2405706 | 5/1979 |
| FR | 2406429 | 5/1979 |
| FR | 2472373 | 7/1981 |
| FR | 2674118 | 9/1992 |
| GB | 2245498 | 1/1992 |
| SU | 610518 | 6/1978 |
| SU | 718097 | 2/1980 |
| SU | 862937 | 9/1981 |
| SU | 897233 | 1/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 A | 2/1992 |
| SU | 1734715 A1 | 5/1992 |
| WO | WO82/01645 | 5/1982 |
| WO | WO87/02572 | 5/1987 |
| WO | WO88/03781 | 6/1988 |
| WO | WO96/29948 | 10/1996 |
| WO | WO 97/47251 | 12/1997 |
| WO | WO01/21083 A1 | 3/2001 |
| WO | WO01/62136 A3 | 8/2001 |
| WO | WO 03/105712 A2 | 12/2003 |
| WO | WO 2003/105712 A2 | 12/2003 |

OTHER PUBLICATIONS

Bone Plates brochure, Vitallium, Mar. 1948.
Dupont Distal Humeral Plates brochure, Howmedica Inc., 1990.
The Arnett—TMP* Titanium Miniplating System brochure, Techmedica, Inc., 1989.
Techmedica Bioengineers Keep Tabs on Your Needs brochure, Techmedica, Inc., 1991.
A Comparison of Unicortical and Bicortical End Screw Attachment of Fracture Fixation Plates, Beaupre et al., *Journal of Orthopaedic Trauma*, vol. 6, No. 3, pp. 294-300, 1992.
Ace 4.5/5.0 mm Titanium Cannulated Screw and Reconstruction Plate System surgical technique brochure, Ace Medical Company, 1992.
Ace 4.5/5.0 mm Titanium Cannulated Screw and Reconstruction Plate System simplified fracture fixation brochure, Ace Medical Company, 1992.
Ace Titanium 3.5/4.0 mm Screw and Plate System with the Ace 3.5 mm Universal Ribbon CT/MRI compatible fixation brochure, Ace Medical Company, 1992.
Treatment of Three- and Four-Part Fractures of the Proximal Humerus with a Modified Cloverleaf Plate, Esser, *Journal of Orthopaedic Trauma*, vol. 8, No. 1, pp. 15-22, 1994.
Ace Symmetry Titanium Upper Extremity Plates surgical technique brochure, Ace Medical Company, 1996.
The Ace Symmetry Titanium Upper Extremity Plates new product release brochure, Ace Medical Company, 1996.
Small Titanium Plates overview page, Synthes, p. 2a-33, Mar. 1997.
Congruent Distal Radius Plate System description, Acumed, Inc., Mar. 4, 1998.
Salvage of Tibial Pilon Fractures Using Fusion of the Ankle with a 90° Cannulated Blade Plate: A Preliminary Report, Morgan et al., *Foot & Ankle International*, vol. 20, No. 6, pp. 375-378, Jun. 1999.
*Scaphoid Protocols Using the Acutrak® Bone Screw System brochure*, Toby, published by Acumed, Inc., Dec. 7, 1999.
Single Unit Osteosynthesis brochure, Surfix Technologies, Sep. 2000.
Supracondylar Cable Plate brochure, Biomet Orthopedics, Inc., 2000.
Principle-Based Internal Fixation of Distal Humerus Fractures, Sanchez-Sotelo et al., *Techniques in Hand & Upper Extremity Surgery*, vol. 5, No. 4, pp. 179-187, Dec. 2001.
Congruent Plate System—The Mayo Clinic Congruent Elbow Plates brochure, Acumed, Inc., May 7, 2002.
Modular Hand System brochure, Acumed, Inc., Aug. 2002.
Modular Hand System brochure, Acumed, Inc., Sep. 2002.
Periarticular Plating System brochure, Zimmer, Inc., 2002.
Jplate Diaphysis Plates for Japanese brochure, Mizuho Co., Ltd., 2002.
An Axially Mobile Plate for Fracture Fixation, Abel et al., *Internal Fixation in Osteoporotic Bone*, pp. 279-283, 2002.
The Use of Interlocked 'Customised' Blade Plates in the Treatment of Metaphyseal Fractures in Patients with Poor Bone Stock, Palmer et al., *Injury, Int. J. Care Injured*, vol. 31, pp. 187-191, 2002.
3.5 mm LCP™ Proximal Humerus Plate technique guide, Synthes (USA), 2002.
Titanium Wire Plate Osteosynthesis System According to Dr. Gahr internet printout, Erothitan Titanimplantate AG, print date Feb. 6, 2003.
Bilder internet printout, Martin GmbH & Co. KG, print date Sep. 5, 2003.
International Search Report for PCT Patent Application Serial No. PCT/US03/22904, Dec. 4, 2003.
The Use of a Locking Custom Contoured Blade Plate for Peri-Articular Nonunions, Harvey et al., *Injury, Int. J. Care Injured*, vol. 34, pp. 111-116, 2003.
Salvage of Distal Tibia Metaphyseal Nonunions With the 90° Cannulated Blade Plate, Chin et al., *Clinical Orthopaedics and Related Research*, No. 409, pp. 241-249, 2003.
Rib Securing Clamped Plate internet printout, Sanatmetal, print date Sep. 22, 2004.
Acromio-Clavicular Plates description page, author and date unknown.
ECT Internal Fracture Fixation brochure, Zimmer, Inc., undated.
ECT Internal Fracture Fixation System order information brochure, Zimmer, Inc., undated.
NexGen Osteotomy System (OS) surgical technique brochure, Zimmer, Inc., undated.
Spider™ and Mini-Spider™ Limited Wrist Fusion System brochure, Kinetics Medical Incorporated, undated.
Spider™ Limited Wrist Fusion System brochure, Kinetics Medical Incorporated, undated.
Zuelzer Hook Plates description page, Codman & Shurtleff, Inc., p. 808, undated.
*Biological Plating: A New Concept to Foster Bone Healing*, Synthes (USA), 1991.

Treatment by Plates of Anteriorly Displaced Distal Radial Fractures, Ducloyer, *Fractures of the Distal Radius*, pp. 148-152, 1995.
Management of Comminuted Distal Radial Fractures, Jupiter et al., *Fractures of the Distal Radius*, pp. 167-183, 1995.
Open Reduction of Intra-Articular Fractures of the Distal Radius, Amadio, *Fractures of the Distal Radius*, pp. 193-202, 1995.
May Anatomical bone Plates: Plates, Bone Screws and Instruments brochure, pp. 3-4 and 10-15, Waldemar Link GmbH & Co., 1995.
Forte Distal Radial Plate System brochure, Zimmer, Inc., 1995.
Design and Biomechanics of a Plate for the Distal Radius, Gesensway et al., *Journal of Hand Surgery*, vol. 20, No. 6, pp. 1021-1027, 1995 (abstract only provided).
*Fractures of the Distal Radius: A Practical Approach to Management*, Fernandez et al., pp. 103-188, 1996.
Titanium Distal Radius Instrument and Implant Set standard contents description pages, Synthes, Mar. 1997.
Prospective Multicenter Trial of a Plate for Dorsal Fixation of Distal Radius Fractures, Ring et al., *The Journal of Hand Surgery*, vol. 22A, No. 5, pp. 777-784, Sep. 1997.
Treatment of Displaced Intra-Articular Fractures of the Distal End of the Radius With Plates, Fitoussi et al., *The Journal of Bone and Joint Surgery*, vol. 79, No. 9, pp. 1303-1312, 1997 (abstract only provided).
The Titanium Distal Radius Plate, technique guide, Synthes (USA), 1997.
TriMed Wrist Fixation System Brochure, TriMed, Inc., 1997.
SCS/D Distal Radius Plate System brochure, Avanta Orthopaedics, 1997.
Intra-Articular Fractures of the Distal Aspect of the Radius, Trumble et al., *Journal of Bone and Joint Surgery*, vol. 80A, No. 4, pp. 582-600, Apr. 1998.
Complications of the AO/ASIF Titanium Distal Radius Plate System (π Plate) in Internal Fixation of the Distal Radius: A Brief Report, Kambouroglou et al., *Journal of Hand Surgery*, vol. 23A, No. 4, pp. 737-741, Jul. 1998.
SCS/V Distal Radius Plate Volar brochure, Avanta Orthopaedics, 1998.
Delayed Rupture of the Flexor Pollicis Longus Tendon After Inappropriate Placement of the π Plate on the Volar Surface of the Distal Radius, Nunley et al., *Journal of Hand Surgery*, vol. 24, No. 6, pp. 1279-1280, Nov. 1999.
TiMAX Pe.R.I. Small Fragment Upper Extremity description pages, DePuy ACE Medical Company, 1999.
The Distal Radius Plate Instrument and Implant Set technique guide, Synthes (USA), 1999.
Outcome Following Nonoperative Treatment of Displaced Distal Radius Fractures in Low-Demand Patients Older Than 60 Years, Young, *Journal of Hand Surgery*, vol. 25A, No. 1, pp. 19-28, Jan. 2000.
Comparison of Three Different Plating Techniques for the Dorsum of the Distal Radius: A Biomechanical Study, Peine et al., *Journal of Hand Surgery*, vol. 25A, No. 1, pp. 29-33, Jan. 2000.
Distal Radial Metaphyseal Forces in an Extrinsic Grip Model: Implications for Postfracture Rehabilitation, Putnam et al., *Journal of Hand Surgery*, vol. 25A, No. 3, pp. 469-475, May 2000.
TriMed Wrist Fixation System internet description pages, TriMed, Inc., 2001.
Titanium Distal Radius Plates description page, Synthes (USA), 2001.
Locon-T Distal Radius Plating System case study and surgical method, Wright Medical Technology, Inc., 2001.
Open Reduction and Internal Fixation of Unstable Distal Radius Fractures: Results Using the Trimed Fixation System, Konrath et al., *Journal of Orthopaedic Trauma*, vol. 16, No. 8, pp. 578-585, 2002.
Locon-T Distal Radius Plating System brochure, Wright Medical Technology, Inc., 2002.
Distal Radius Fracture, Tornetta, *Journal of Orthopaedic Trauma*, vol. 16, No. 8, pp. 608-611, 2002.
Comparison of Different Distal Radius Dorsal and Volar Fracture Fixation Plates: A Biomechanical Study, Osada et al., *Journal of Hand Surgery*, vol. 28A, No. 1, pp. 94-104, Jan. 2003.
*Tendon Function and Morphology Related to Material and Design of Plates For Distal Radius Fracture Fixation: Canine Forelimb Model*, Turner et al., Orthopaedic Research Society, Feb. 2003.
Fractures of the Distal Aspect of the Radius: Changes in Treatment Over the Past Two Decades, Simic, *Journal of Bone and Joint Surgery*, vol. 85-A, No. 3, pp. 552-564, Mar. 2003.
Palmar Plate Fixation of AO Type C2 Fracture of Distal Radius Using a Locking Compression Plate—A Biomechanical Study in a Cadaveric Model, Leung et al., *Journal of Hand Surgery*, vol. 28B, No. 3, pp. 263-266, Jun. 2003.
Functional Outcome and Complications Following Two Types of Dorsal Plating for Unstable Fractures of the Distal Part of the Radius, Rozental et al., *Journal of Bone and Joint Surgery*, vol. 85, No. 10, pp. 1956-1960, 2003 (abstract only provided).
*Fixation of Unstable Fractures of the Volar Rim of the Distal Radius with a Volar Buttress Pin®*, Hooker et al., 2003.
Results of Palmar Plating of the Lunate Facet Combined with External Fixation for the Treatment of High-Energy Compression Fractures of the Distal Radius, Ruch et al., *J. Orthop. Trauma*, Vo. 18, No. 1, pp. 28-33, Jan. 2004.
Synthes Volar Distal Radius Locking Plate internet description page, Orthocopia, LLC, 2004.
VAL Plate description page, US Implants, undated.
Esser Complete Distal Radius Plate System, undated.
Proximal Humerus Fractures operative technique, Esser, undated.
Biomechanical Evaluation of the Schuhli Nut, Kolodziej, et al., *Clinical Orthopaedics and Related Research*, vol. 347, pp. 79-85, Feb. 1998.
Internal Fixation in Osteoporotic Bone, An, Y.H., p. 83, 2002.
Zespol Bone Screws, in *Mikromed—Catalogue 2004* (Nov. 2004), available at http://www.mikromed.pl/katalog/Main/main_eng.htm and http://www.mikromed.pl/katalog/zespol_eng/wkrety.htm.
Zespol Bone Plates, in *Mikromed—Catalogue 2004* (Nov. 2004), available at http://www.mikromed.pl/katalog/Main/main_eng.htm and http://www.mikromed.pl/katalog/zespol_eng/plytki.htm.
SmartLock Locking Screw Technology, advertisement, *The Journal of Hand Surgery*, vol. 30A, No. 1, Jan. 2005.
MIfx Dorsal IM Plate, brochure, DVO Extremity Solutions, Sep. 2005.

* cited by examiner

DEFORMABLE BONE PLATES

CROSS-REFERENCE TO PRIORITY APPLICATIONS

This application is based upon and claims the benefit under 35 U.S.C. § 119(e) of the following U.S. provisional patent applications: Ser. No. 60/427,908, filed Nov. 19, 2002; and Ser. No. 60/512,136, filed Oct. 17, 2003. Each of these provisional patent applications is incorporated herein by reference in its entirety for all purposes.

CROSS-REFERENCES TO OTHER APPLICATIONS

This application incorporates by reference in their entirety for all purposes the following U.S. patent applications: Ser. No. 10/716,719, filed Nov. 19, 2003 now U.S. Pat. No. 7,090,676; Ser. No. 10/717,401, filed Nov. 19, 2003; Ser. No. 10/717,015, filed Nov. 19, 2003; and Ser. No. 10/717,399, filed Nov. 19, 2003.

This application incorporates by reference in their entirety for all purposes the following U.S. provisional patent applications: Ser. No. 60/427,910, filed Nov. 19, 2002; Ser. No. 60/512,111, filed Oct. 17, 2003; Ser. No. 60/512,322, filed Oct. 17, 2003; and Ser. No. 60/512,323, filed Oct. 17, 2003.

This application incorporates by reference in its entirety for all purposes PCT Patent Application Serial No. PCT/US02/18623, filed Jun. 10, 2002.

FIELD OF THE INVENTION

The invention relates to bone plates. More specifically, the invention relates to bone plates configured to be deformed after being secured to bone.

BACKGROUND

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become damaged should be repaired promptly and properly. Typically, a fractured or cut bone is treated using a fixation device, which reinforces the bone and keeps it aligned during healing. Fixation devices may include external fixation devices (such as casts and fixators) and/or internal fixation devices (such as bone plates, nails/rods, and bone screws), among others.

Bone plates are sturdy internal devices, usually made of metal, that mount directly to the bone adjacent the fracture (or osteotomy). To use a bone plate to repair a discontinuity of a bone, a surgeon typically (1) selects an appropriate plate, (2) reduces the discontinuity (e.g., sets the fracture), and (3) fastens the plate to bone portions disposed on opposite sides of the discontinuity using suitable fasteners, such as screws and/or wires, so that the bone portions are fixed in position.

Despite direct access to the bone portions when applying a bone plate, the surgeon may have difficulty fixing the bone portions with the correct alignment. For example, one or more of the bone portions may be relatively small and/or displaced from the bone plate. As a specific example, in fixation of a fracture of a phalanx (a finger bone), a distal bone portion(s) adjacent the fracture may be difficult to position properly. Accordingly, the finger bone may be fixed improperly so that the corresponding finger heals in a crooked configuration. More generally, during attachment of any bone plate, fasteners may be misplaced or misdirected so that bone portions move away from a desired positioning when the fasteners are advanced into engagement with the bone plate. Accordingly, the relative position of the bone portions may need to be adjusted after the bone plate has been secured to a bone to achieve proper reduction of a fracture.

SUMMARY OF THE INVENTION

The invention provides bone plates configured to be deformed after being secured to bone, apparatus including the bone plates, and methods of using the bone plates to fix bones.

DETAILED DESCRIPTION

The invention provides bone plates configured to be deformed after being secured to bone, apparatus including the bone plates, and methods of using the bone plates to fix bones.

The bone plate may include one, two, or more anchor portions configured to be secured to bone. In some examples, the bone plate may include two or more anchor portions configured to be secured to opposing sides of a bone continuity, such as a fracture (e.g., due to an injury), a cut (e.g., due to an osteotomy), or a joint, among others.

The bone plate may include one or more predefined deformation regions at which the bone plate may be selectively deformed, to bend and/or twist the bone plate. The deformation region(s) may be disposed between anchor portions in a bridge region of the bone plate, and/or within one or more of the anchor portions, among others. The deformation region may be selectively deformable due to a difference in width, thickness, shape, composition, crystal structure, and/or treatment, among others, of the deformation region relative to other regions of the bone plate, particularly flanking regions and/or the anchor portions. In some embodiments, the deformation region may be a ridge configured to be spaced from a bone when the anchor portions are apposed to the bone.

The bone plate may be configured to be engaged with one or more tools configured to deform the deformation region. In some embodiments, the one or more tools may grip the bone plate adjacent the deformation region, such as when the deformation region is a ridge. In some embodiments, the one or more tools may be received by a receiver structure of the bone plate, such as one or more openings (and/or protrusions) of the bone plate. The one or more openings may be nonthreaded, or threaded for threaded engagement with the one or more tools, among others. The one or more openings may be a pair of openings that flank the deformation region. In some embodiments, the one Or more tools may be threaded for threaded for connection to the bone plate, and may include a handle configured to be grasped by a user to exert a deforming torque on the bone plate.

The deformable bone plates, as described herein, may be used to perform methods of bone fixation. The methods may include a step of securing a deformable bone plate to at least one bone and then deforming the secured bone plate. The bone plate may be secured to different bone regions so that the step of deforming the secured bone plate adjusts a relative angular and/or translational disposition of the different bone regions. For example, the bone plate may be secured to a fractured bone, so that the step of deforming the secured bone plate reduces a fracture of the bone.

Deformable bone plates, as described herein, may be attached to or otherwise associated with bone using any suitable method or procedure. For example, a surgeon may (1) select an appropriate plate, (2) reduce (set) any fracture (s) or other discontinuities in the bone (at least partially), (3) fasten the plate to opposite sides of the fracture using suitable fasteners, such as screws, pins, and/or wires, to fix the bone, and (4) deform the plate to adjust reduction of the fracture. These steps may be performed manually and/or mechanically, for example, using a guide system as described in the following patent application, which is incorporated herein by reference in its entirety for all purposes: U.S. patent application Ser. No. 10/717,401, filed Nov. 19, 2003.

Figure 1:
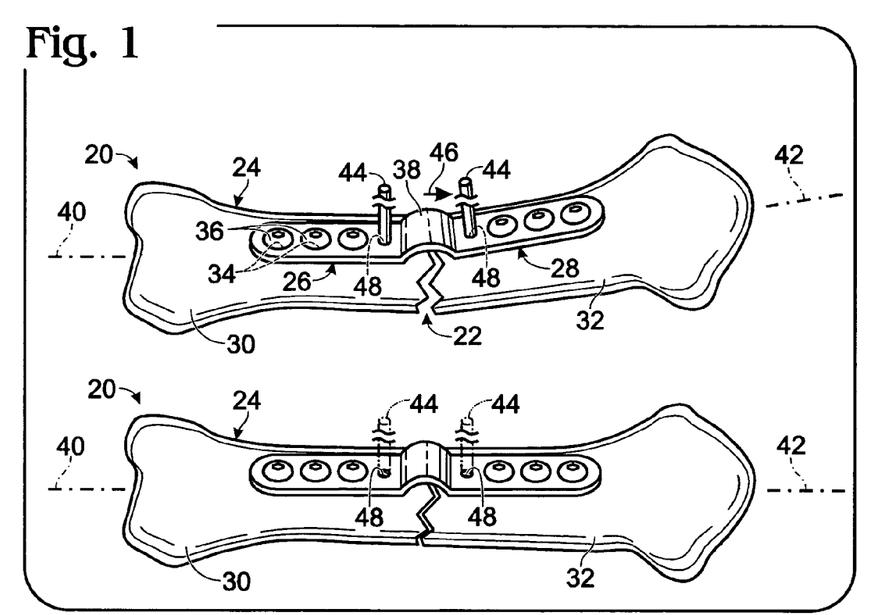
FIG. 1 is a pair of views of a fractured bone (A) before and (B) after reduction of its fracture by deformation of a bone plate affixed to the fractured bone, in accordance with the present teachings.

FIG. 1 shows a fractured bone 20(A) before and (B) after adjusting reduction of its fracture 22 (upper and lower portions of the figure, respectively) by deformation of a bone plate 24 affixed to the fractured bone.

Bone plate 24 may include first and second anchor portions 26, 28 configured to be secured to respective regions 30, 32 of bone 20. Each anchor portion may include a connective feature, such as one more openings 34 for receiving fasteners, such as bone screws 36. Each opening may be threaded or nonthreaded. The bone plate also may include a deformation region 38 at which the bone plate may be deformed selectively. In this example, deformation region 38 is disposed adjacent fracture 22, between the anchor portions and spaced from bone 20.

The upper portion (Panel A) of FIG. 1 shows bone 20 with bone regions 30, 32 misaligned. In particular, respective bone region axes 40, 42 are not substantially parallel. However, bone plate 24 may be deformed at deformation region 38 by applying a deforming torque to the bone plate. Tools 44 may engage the bone plate so that a surgeon may apply a suitable directional force 46 on the tools to create the deforming torque. Tools 44 may be gripping tools that grip the bone plate. Alternatively, or in addition, the tools may be handles configured to be received by one or more receiver structures 48 of the bone plate. In some embodiments, tools 44 and receiver structures 48 may be configured for threaded engagement.

The lower portion (Panel B) of FIG. 1 shows bone 20 after adjustment of reduction of the fracture, so that bone regions 30, 32 are substantially aligned. In particular, bone axes 40, 42 are substantially parallel. After deformation of the bone plate, handles 44 may be removed, as indicated by the present illustration with the handles in phantom outline. Furthermore, receiver structures 48 may receive plugs to fill any holes or even out any discontinuities, or fasteners to further secure the bone plate to the bone.

Further aspects of the invention are described in the following sections, including (I) an overview of general aspects of deformable bone plates, (II) selected aspects of deformable bone plates, and (III) examples.

I. Overview of General Aspects of Deformable Bone Plates

Bone plates as described herein generally comprise any relatively low-profile (or plate-like) fixation device configured to stabilize at least one bone by attachment to the bone. The fixation device may be configured to span a bone discontinuity (such as a fracture, a cut, a bone joint, etc.) so that the fixation device fixes the relative dispositions of bone portions disposed on opposing sides of the bone discontinuity. The fixation device generally is configured to be disposed in contact with an outer surface of the bone and thus may be positioned at least substantially exterior to the bone. The bone plate may be left in place permanently or removed after the associated bone has partially or completely healed.

The bone plates may be of a sturdy yet malleable construction. Generally, the bone plates should be stiffer and stronger than the section of bone spanned by the plates, yet flexible (e.g., springy) enough not to strain the bone significantly. Suitable materials may be biocompatible materials (such as titanium or titanium alloys, cobalt chromium, stainless steel, plastic, ceramic, etc.) and/or bioabsorbable materials (such as polygalactic acid (PGA), polylactic acid (PLA), copolymers thereof, etc.), among others.

The bone plates may be configured to reduce irritation to the bone and surrounding tissue. For example, the bone plates may be formed of a biocompatible material, as described above. In addition, the bone plates may have a low and/or feathered profile to reduce their protrusion into adjacent tissue and rounded, burr-free surfaces to reduce the effects of such protrusion.

The bone plates may have at least one, and generally two or more, distinct anchor (or bone-attachment) portions, configured to be secured to a bone. Each anchor portion may be structured for a specific portion of a bone, generally to fit against a surface region of bone adjacent a bone discontinuity. For example, the bone plates may include a proximal anchor portion for attachment to a more proximal region of a bone, and a distal anchor portion for attachment to a more distal region of the same bone. In some embodiments, the bone plates may include a support (or buttress) portion connected to an anchor portion. The support portion may lack connective features that permit a direct connection of the support portion to the bone with one or more fasteners. Such a support portion may limit movement of a bone fragment using contact between the support portion and the fragment, and may include projections or prongs to engage the fragment more effectively.

The bone plates may include a bridge region that is disposed between and joins anchor portions. Accordingly, the bridge region may be an intermediate plate segment disposed between flanking plate segments. The bridge region may be configured to be disposed adjacent a bone discontinuity when the anchor portions are secured to bone regions disposed oh opposing sides of a bone discontinuity.

The bridge region may have any suitable structure. In some embodiments, the bridge region may be configured as a deformation region at which the bone plate is deformed. Accordingly, the bridge region may differ structurally from the anchor portions in shape, one or more characteristic dimensions, composition, etc. Further aspects of deformation regions and bridge regions are described below in Sections II and III.

The bone plates described herein may be sized and shaped to conform to particular portions of a bone (or bones). The plates may be generally elongate, with a length L, a width W, and a thickness T. Here, length $L \geq$ width $W \geq$ thickness T. In use, the long axis of the bone plates may be aligned with the long axis of the corresponding bone or may extend obliquely or transversely relative to the bone's long axis. The length and/or width of the bone plates may be varied according to the intended use, for example, to match the plates with a preselected region of bone(s) and/or a particular injury to the bone. For example, the plates may be generally linear for use on the shaft of a long bone or may have a nonlinear shape, such as for use near an end of a bone. In some embodiments, the plates may be generally T-shaped, including an axial portion, for attachment to a shaft portion of a bone, and a transverse portion connected to the axial portion, to provide a wider platform for attachment near an end of the bone. In some embodiments, each bone plate may be configured for use on both sides of the body, such as when the bone plates are bilaterally symmetrical. In some embodiments, each bone plate may be asymmetrical and configured for use on either the left or the right side of the body.

The bone plates described herein may be configured for use on any suitable bone of the human body and/or of another vertebrate species. Exemplary bones may include bones of the arms (radius, ulna, humerus), legs (femur, tibia, fibula, patella), hands, feet, the vertebrae, scapulas, pelvic bones, cranial bones, the ribs and/or the clavicles, among others. Particular examples where deformable bone plates may be suitable include a phalanx, the distal radius, and the distal tibia.

The bone plates may include inner (bone-facing) and outer (bone-opposing) surfaces. One or both of these surfaces may be contoured generally to follow a surface of a target bone (or bones) for which the bone plates are intended, so that the bone plates maintain a low profile and fit onto the bone(s). For example, the inner surface of a plate may be generally complementary in contour to the bone surface. The outer surface may correspond in contour to the bone surface and may be generally complementary to the inner surface of the plate.

The thickness of the bone plates is defined by the distance between the inner and outer surfaces of the plates. The thickness of the plates may vary between plates and/or within the plates, according to the intended use. For example, thinner plates may be configured for use on a smaller bone and/or on a bone or bone region where soft tissue irritation is a greater concern. Thickness may be varied within the plates. For example, the plates may become thinner as they extend over protrusions (such as processes, condyles, tuberosities, and/or the like), reducing their profile and/or rigidity, among others. The thickness of the plates also may be varied to facilitate use, for example, to make the plates thinner where they typically need to be deformed by bending and/or twisting the plates.

The bone plates generally include a plurality of openings. The openings may be adapted to receive fasteners for securing the plates to bone. Alternatively, or in addition, the openings may be adapted to alter the local rigidity of the plates, to permit the plates to be manipulated with a tool (such as a coupled handle), and/or to facilitate blood flow to the fracture or surgical site to promote healing, among others.

The openings may have any suitable positions, sizes, and/or densities within each portion of a bone plate. The openings may be arrayed generally in a line along a portion Of the plate, for example, centered across the width of the plate. Alternatively, the openings may be arranged nonlinearly in the plate portion, for example, disposed in a staggered arrangement. In some embodiments, the openings may be configured so that a set of bone screws can be directed along nonparallel paths, for example, to increase the purchase of the set of bone screws on bone. Further aspects of openings configured to direct bone screws along nonparallel paths are included the following patent application, which is incorporated herein by reference: U.S. Provisional Patent Application Ser. No. 60/512,111, filed Oct. 17, 2003.

The openings may have any suitable shape and structure. Exemplary shapes may include circular, elliptical, rectangular, elongate, etc. The openings may include counterbores configured, for example, to receive a head of a bone screw. The openings may be threaded or nonthreaded, and each bone plate may include one or more threaded and/or nonthreaded openings. In some embodiments, the plates may include one or a plurality of elongate openings (slots) extending axially and/or transversely along each bone plate. The slots may include counterbores that provide compression when bone screws are advanced against the counterbores. Alternatively, or in addition, the slots may be used to adjust the position of bone plates and/or plate portions relative to bone before the plates are fully secured to the bone. Further aspects of openings or slots that may be suitable for deformable bone plates are described in more detail in the following patent applications, which are incorporated herein by: PCT Patent Application Serial No. PCT/US02/18623, filed Jun. 10, 2002; and U.S. patent application Ser. No. 10/717,015, filed Nov. 19, 2003.

The fasteners generally comprise any mechanism for affixing a bone plate to a bone, including screws, pins, and wires, among others. A preferred fastener is a bone screw, including unicortical, bicortical, and/or cancellous bone screws. Unicortical and bicortical bone screws typically have relatively small threads for use in hard bone, such as typically found in the shaft portion of a bone, whereas cancellous bone screws typically have relatively larger threads for use in soft bone, such as typically found near the ends (periarticular regions) of a long bone. Unicortical bone screws penetrate the bone cortex once, adjacent the bone plate. Bicortical bone screws penetrate the bone cortex twice, adjacent the bone plate and opposite the bone plate. Generally, unicortical screws provide less support than bicortical screws, because they penetrate less cortex. The size and shape of the fasteners may be selected based on the size, shape, and disposition of the openings, or vice versa. For example, unicortical bone screws may be suitable with particular arrangements of openings.

The bone plates generally may be formed unitarily, as one piece, or as two or more pieces. Deformable bone plates of two or more pieces may be configured to include both a deformation region and a movable joint. Further aspects of bone plates with movable joints are described in the following patent application, which is incorporated here by reference: U.S. patent application Ser. No. 10/716,719, filed Nov. 19, 2003 now U.S. Pat. No. 7,090,676.

II. Selected Aspects of Deformable Bone Plates

Deformable bone plates generally comprise any bone plate in which a region of the bone plate is configured to be deformed before, while, and/or after the bone plate is secured to bone, to change the overall shape (and/or size) of the bone plate. The bone plate may be deformable at least substantially in a predefined deformation region. The deformation region may be a bridge region disposed between different anchor and/or support portions of the plate. Accordingly, deformation of the bone plate may bend, twist, and/or translate the anchor and/or support portions relative to one another so that their relative angular and/or translational dispositions are changed. The plates may be bent using any suitable method, including manually and/or with a deformation tool, among others, as described below.

II.A Deformation Region

The deformation region is configured to predefine a site of bending and/or twisting within the bone plate when torque is applied to the bone plate. Accordingly, the deformation region may be created by differences in one or more aspects of the deformation region relative to flanking segments (such as anchor portions) of the bone plate. The aspect(s) of the deformation region that may be different includes a characteristic dimension, the shape, the composition, and/or a treatment, among others.

The characteristic dimension may be the thickness and/or width of the deformation region. Accordingly, the deformation region may be thinner and/or narrower than flanking regions of the bone plate. In some embodiments, the deformation region may include at least one groove or depression. The groove or depression may extend transversely on the bone plate.

The shape may include any contour defined by a surface of the deformation region. Differences in shape may include a bent contour (angled and/or curved) in profile, such as a ridge, one or more openings, and/or the like. The shape may be configured to direct deforming forces, received from tools, to the deformation region.

The composition refers to the material that forms the deformation region. An altered composition of the deformation region may be produced, for example, by fabricating the bone plate with materials of different strengths/flexibilities along the length of the plate. When the bone plate is formed of metal, the deformation region may be formed of a different metal or metal alloy composition relative to adjacent segments of the bone plate. In some examples, the plate may be fabricated as segments that are joined after fabrication, or the plate may be cast as segments with different compositions within a single mold, among others.

The treatment may be any differential processing of the deformation region. Such differential processing may include pre-bending, scoring, compressing, stretching, heating, etc. For example, the deformation region may be pre-bent so that this region is favored when torque is applied to the plate. Pre-bending may increase the flexibility of the deformation region or direct a greater fraction of the torque to the deformation site. In some embodiments, the deformation region may be annealed differently than flanking segments of the bone plate. Differential annealing may change the crystal structure of the deformation region selectively relative to flanking segments of the bone plate.

II.B Tool Engagement Sites

The bone plate may include one or more tool-engagement sites. The tool-engagement sites may be any region(s) of the bone plate configured to couple a deformation tool to the bone plate. The tool-engagement sites may flank the deformation region and/or may be included in this region. The disposition of the tool-engagement sites may define the position of the deformation region within the bone plate, by selectively directing deforming forces to this region. Accordingly, the bone plate may have a plurality of tool-engagement sites that may be engaged selectively, such as pairwise, to deform different regions of the plate.

In some embodiments, the tool-engagement sites may be configured to be spaced from bone when the bone plate is secured to bone, with flanking segments of the bone plate apposed to bone. Accordingly, the deformation region may include a ridge at which a tool (or tools) can grip the bone plate, generally by opposing contact with inner and outer surfaces of the bone plate. In some embodiments, deformation of a ridge may adjust the translational spacing of anchor portions, for example, by increasing or decreasing the spacing of the ridge's apex from bone.

In some embodiments, the tool engagement sites may include a receiver structure (or structures) in, on, or about which a tool (or tools) can be received. The receiver structure may include an opening or any other space at which a tool can apply a torque to the bone plate. The opening may be a recess or hole defined by an edge of the bone plate, by an inner surface of the plate, by an outer surface of the plate, by inner and outer surfaces, and/or the like. For example, the opening may be configured to receive a deformation tool that has a tip configured to fit into the opening. Alternatively, or in addition, a tool-engagement site may be defined by an anchor portion of the bone plate, for example, an opening in the anchor portion that can be engaged by a deformation tool received threadedly or nonthreadedly in the opening. The opening also may be configured to receive a fastener, such as a bone screw, for securing the bone plate to bone. The opening thus may be used alternately for deformation and securing, or may be configured to be used concurrently for both operations.

II.C Deformation Tools

A deformation tool for use with a deformable bone plate may have any suitable structure and size. The tool may include an engagement region configured to engage the bone plate, and an interface region configured to interface with a person or another device (such as another tool or a machine). The engagement region may have any suitable feature(s) that permits and facilitates engagement with the bone plate. Such features may include a threaded section, serrations, opposing jaws, bumps, a dovetail configuration, etc. The engagement region may be configured so that the tool extends at least substantially in a direction normal from the outer surface of the bone plate or from a plane defined by the bone plate, when the engagement region is engaged with an engagement site of the bone plate. The interface region may be configured to be grasped by a person, and thus may be considered a handle. Accordingly, the interface region may be knurled and/or may include other surface features that facilitate engagement with a hand. The tool may have any suitable length that permits the interface region to be grasped or engaged and/or to apply a suitable torque. In some embodiments, the length may be greater than one-third, one-half, one, two, three, five, ten, or more times the distance between one or more of the tool engagement sites and the deformation region. In the same and/or other embodiments, the length may be greater than one-third, one-half, one, two, three, five, ten, or more times the total length of the bone plate for which the tool is configured. In general, the length of the tool may be increased with larger and/or sturdier bone plates for which a greater torque may be needed.

II.D Kits

A deformable bone plate may be supplied in a kit. The kit may include at least one bone plate, one or more bone fasteners for securing the bone plate to bone, one or more tools configured to deform the bone plate, and/or instructions for use of the kit. Different bone plates of the kit may be configured for use on different bones, different regions of bones, different sides of the body, and/or the like. Accordingly, the bone plates (and/or fasteners/tools) may include indicia that identify and distinguish different bone plates (and/or fasteners/tools). The tools configured to deform the bone plate may differ in type (e.g., handles versus pliers), size (e.g., long versus short), and/or other characteristics.

III. EXAMPLES

The following examples describe selected aspects and embodiments of the invention, including deformable bone plates and associated tools, and exemplary methods of using deformable bone plates to fix bones. These examples are included for illustration and are not intended to limit or define the entire scope of the invention.

Example 1

Fixation of a Fractured Phalanx Using Deformable Bone Plates

This example describes deformable bone plates and associated tools for fixing a fractured phalanx and adjusting reduction of its fracture; see FIGS. 2 to 10.

Figure 2:
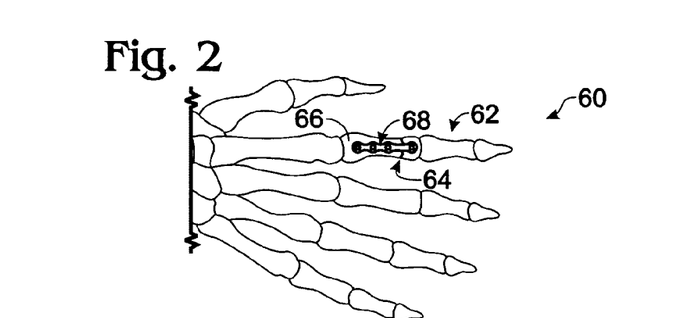
FIG. 2 is a dorsal view of the distal bones of the right hand, particularly the metacarpals and the phalanges, with a first example of a deformable bone plate secured to a proximal phalanx of the phalanges and fixing a fracture thereof, in accordance with the present teachings.

FIG. 2 shows a dorsal view of the distal bones of right hand 60 with the forefinger 62 exhibiting a distal fracture 64 of proximal phalanx 66. Fractured phalanx 66 may be fixed with a deformable bone plate 68. Deformation of bone plate 68 after securing the bone plate to phalanx 66 may improve reduction of distal fracture 64 so that the pieces of this phalanx regain a more natural alignment. Observation of the disposition of the forefinger may be used to guide the deformation. In particular, a minor mis-alignment within fractured proximal phalanx 66 may translate into an easily detectable change in the forefinger disposition.

Figure 3:
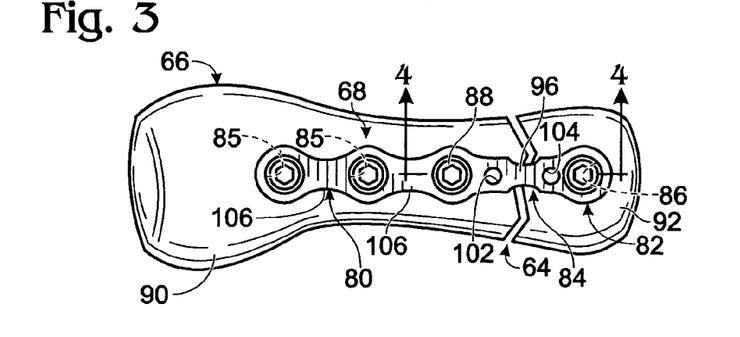
FIG. 3 is a dorsal view of the proximal phalanx and the deformable bone plate of FIG. 2 before deformation of the bone plate, in accordance with the present teachings.

FIG. 3 shows deformable bone plate 68 secured to fractured phalanx 66 before deformation of the bone plate. Bone plate 68 may include proximal and distal anchor portions 80, 82, respectively, joined by a deformable bridge region 84. Anchor portions 80, 82 may define one or more proximal and distal openings 85, 86, respectively, each of which may be threaded or nonthreaded. The openings may receive bone screws 88 for securing the bone plate to proximal phalanx 66 on opposite sides of fracture 64. In particular, proximal anchor portion 80 of the bone plate may be secured to proximal bone region 90, and distal anchor portion 82 may be secured to distal bone region 92. Bridge region 84 may be disposed adjacent fracture 64.

Bridge region 84 may be configured so that deforming forces exerted on the bone plate are directed to a deformation region 96 of the bridge region. In the present illustration, the deformation region is a narrowed segment of the bone plate. Deforming forces may be exerted on bone plate 68 through additional openings 102, 104 in the bone plate. Each additional opening may be configured to be engaged by a tool so that the tools can direct deforming forces to deformation region 96. The additional openings may be threaded or nonthreaded. In some embodiments, openings 85 and/or 86 may be used for tool engagement.

The bone plate also may include one or more additional deformation regions 106 configured for selective deformation. Each additional deformation region may be selectively deformed by application of a deforming force to these regions, before, during, and/or after securing the bone plate to the bone.

Figure 4:
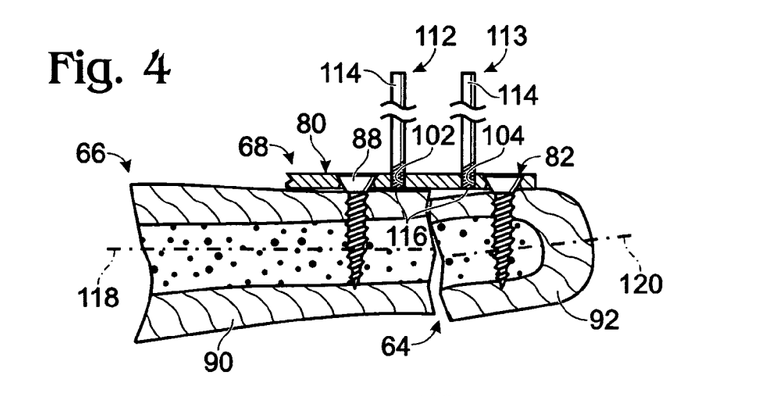
FIG. 4 is a fragmentary sectional view of the fractured proximal phalanx and deformable bone plate of FIG. 3, viewed generally along line 4—4 of FIG. 3, with handles attached to the bone plate and before adjusting reduction of the phalanx fracture, in accordance with the present teachings.

FIG. 4 shows a sectional view of fractured phalanx 66 and bone plate 68 before adjusting reduction of fracture 64. Tools 112, 113 configured to deform the bone plate may be coupled to the bone plate so that the tools provide handles 114 that can be grasped by hand. The handles may be, for example, smaller handles configured to be gripped between a thumb and one or more fingers, or larger handles configured to be gripped by the fingers and palm. Distal ends 116 of the tools may be disposed in threaded engagement with openings 102, 104 of the bone plate. Proximal and distal bone regions 90, 92 may have their respective axes 118, 120 disposed out of alignment.

Figure 5:
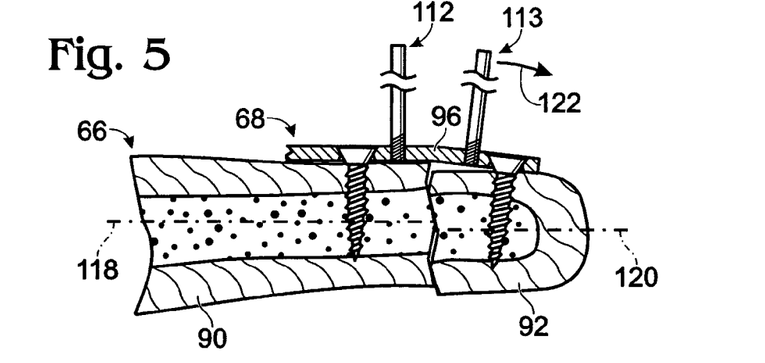
FIG. 5 is a fragmentary sectional view of the fractured proximal phalanx, deformable bone plate, and handles of FIG. 4 after applying a torque to the bone plate with the handles, so that the bone plate is deformed to adjust reduction of the fracture of the proximal phalanx, in accordance with the present teachings.

FIG. 5 shows fractured phalanx 66 after deformation of bone plate 68 at deformation region 96. In the present illustration, the upper ends of tools 112, 113 have been rotated apart, shown at 122, using a hand or another tool. Relative movement of the tools may apply a torque to the deformation region 96, which responds here by bending upward in this view. As a result, distal bone region 92 is rotated clockwise, so that bone region axes 118, 120 are disposed in a more parallel relationship, to improve the alignment of bone portions 90, 92. Axes 118, 120 may be somewhat displaced, as shown here, so that bone regions 90, 92 are offset from each other. Alternatively, the axes may be moved to a substantially collinear configuration.

Figure 6:
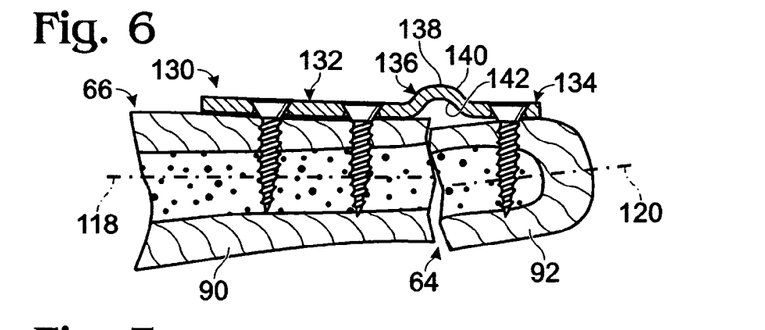
FIG. 6 is fragmentary sectional view of the fractured proximal phalanx of FIG. 4 with a second example of a deformable bone plate secured to the proximal phalanx before adjusting reduction of the phalanx fracture, in accordance with the present teachings.

FIG. 6 shows a second example of a deformable bone plate 130 secured to fractured phalanx 66 with mis-alignment of bone region axes 118, 120. Bone plate 130 may include proximal and distal anchor portions 132, 134 secured to bone regions 90, 92, respectively. A bridge region 136 may join the anchor portions and may be disposed adjacent fracture 64. Bridge region 136 may be configured to be spaced from bone, as shown here. Bridge region 136 may include a deformation region 138 in the form of a ridge with an apex and flanking sides disposed at an incline relative to a plane defined by the plate. The deformation region 138 may be configured to be gripped by tools on opposing surfaces 140, 142 of the bone plate. The deformation region 138 may be selectively deformed at one or more positions along the deformation region. Such selective deformation may adjust the angular disposition and/or the translational disposition of the anchor portions and thus the bone portions. A bend introduced at any position within the deformation region may adjust the angular disposition. However, adjustment of the translational disposition may involve introduction of a plurality of compensatory bends in the deformation region, to adjust the spacing of the apex from bone.

Figure 7:
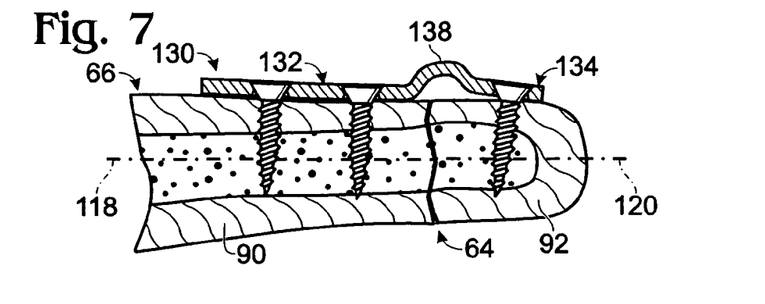
FIG. 7 is a fragmentary sectional view of the fractured proximal phalanx and deformable bone plate of FIG. 6 after adjusting reduction of the fracture by deformation of the bone plate with gripping tools, in accordance with the present teachings.

FIG. 7 shows fractured phalanx 66 and bone plate 130 with improved alignment of bone region axes 118, 120 by deformation of the bone plate at deformation region 138. Bone regions 90, 92 are spaced and aligned in accordance with a natural spacing and alignment of these regions.

Figure 8:
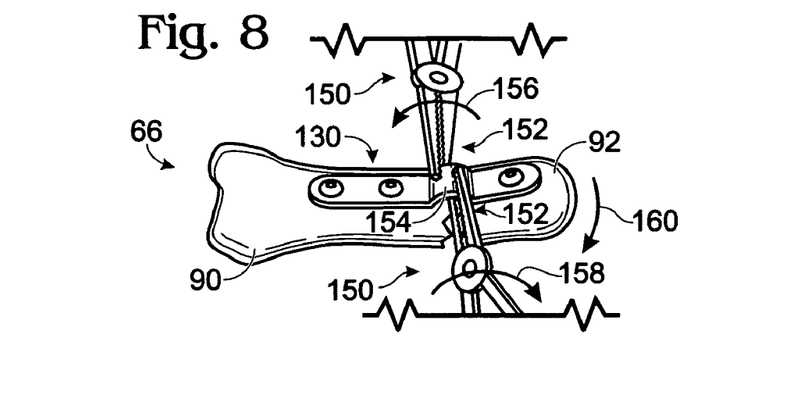
FIG. 8 is a View of the fractured proximal phalanx and deformable bone plate of FIG. 6 being gripped with gripping tools and before adjusting reduction of the phalanx fracture by application of a torque to the bone plate using the gripping tools, in accordance with the present teachings.

FIG. 8 shows fractured phalanx 66 with bone plate 130 secured to the phalanx and gripped with gripping tools 150. The gripping tools may be towel clamps or pliers configured to opposingly grip the bone plate. The gripping tools may have an adjustable and a locked configuration, or only an adjustable configuration. Each gripping tool may include jaws 152 that engage the bone plate on the inner and outer surfaces of the bone plate. Accordingly, one of the jaws may be configured to be thin enough to slide between the bone plate and bone, as shown here. The gripping tools may be connected to each other or may be separate. In some embodiments, the gripping tools may be connected by articulating handles that permit bending and/or twisting deformation of the bone plate. The gripping tools may be placed on opposing sides of a desired site 154 of deformation within the bone plate. Opposing torques, shown at 156, 158 exerted on the deformation site with the gripping tools may deform the plate and adjust the disposition of the bone portions relative to each other, shown at 160.

Figure 9:
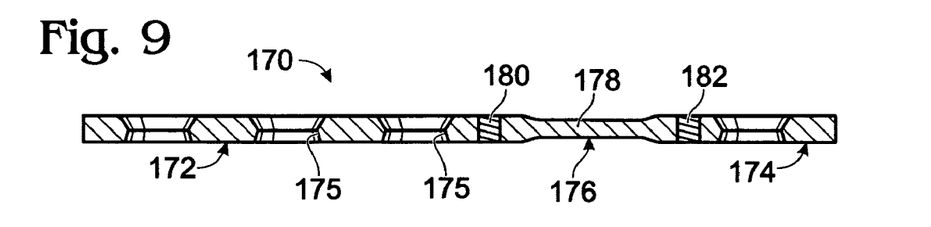
FIG. 9 is a longitudinal sectional view of a third example of a deformable bone plate in which the bone plate has a thinned deformation region, in accordance with the present teachings.

FIG. 9 shows a third example of a deformable bone plate 170. Bone plate 170 may include a proximal anchor portion 172 and a distal anchor portion 174 defining a plurality of openings 175. The bone plate also may include a bridge region 176 joining the anchor portions. Bridge region 176 may be thinned relative to the anchor portions to create deformation region 178. Bone plate 170 also may include threaded tool-engagement sites 180, 182 disposed on opposing sides of the bridge region. In some embodiments, deformation region 178 may not differ substantially from other portions of the bone plate structurally, but may be selectively deformed by deforming forces directed to the deformation region based on its position within the bone plate.

Figure 10:
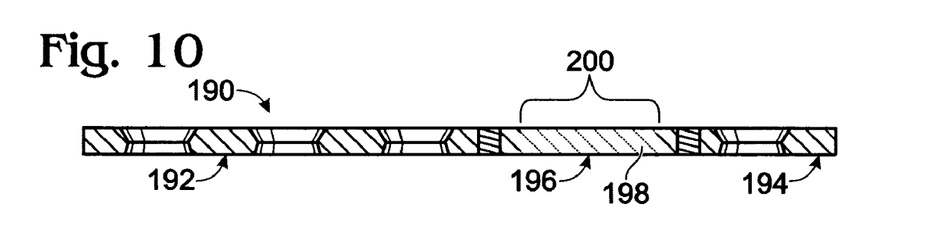
FIG. 10 is a longitudinal sectional view of a fourth example of a deformable bone plate in which the bone plate has a deformation region produced by differentially annealing the bone plate, in accordance with the present teachings.

FIG. 10 shows a fourth example of a deformable bone plate 190. Bone plate 190 may include a proximal anchor portion 192 and a distal anchor portion 194 joined by a bridge region 196. Bridge region 196 may include a deformation region 198 produced by differential treatment of the deformation region, indicated at 200, such as by differential annealing of segments of the bone plate. Alternatively, or in addition, deformation region 198 may have a different composition than other segments of the bone plate.

Example 2

Fixation of a Fractured Radius with a Deformable Bone Plate

Figure 11:
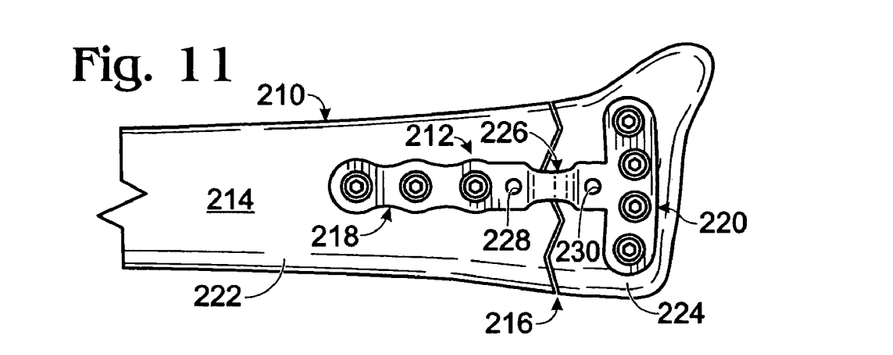
FIG. 11 is a volar view of a fractured distal radius fixed with a fifth example of a deformable bone plate, in accordance with the present teachings.
Figure 12:
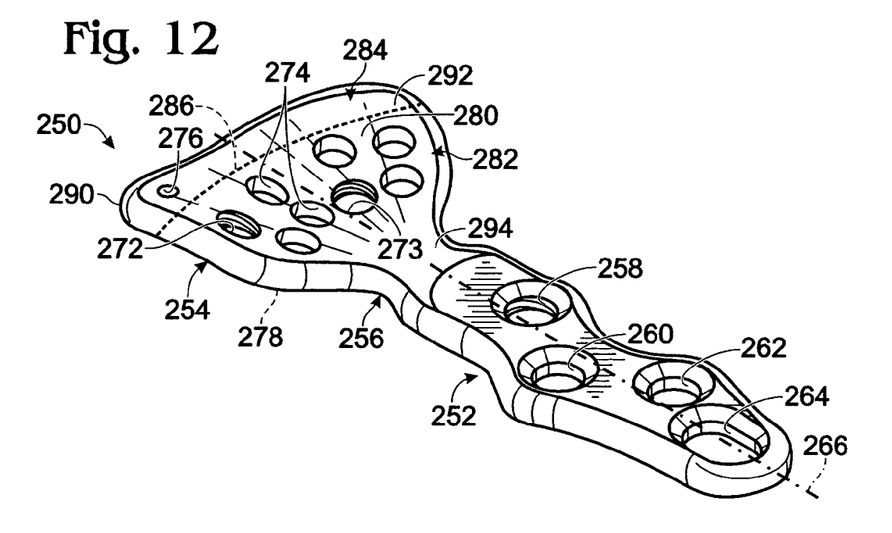
FIG. 12 is a view of a sixth example of a deformable bone plate, in accordance with the present teachings.
Figure 13:
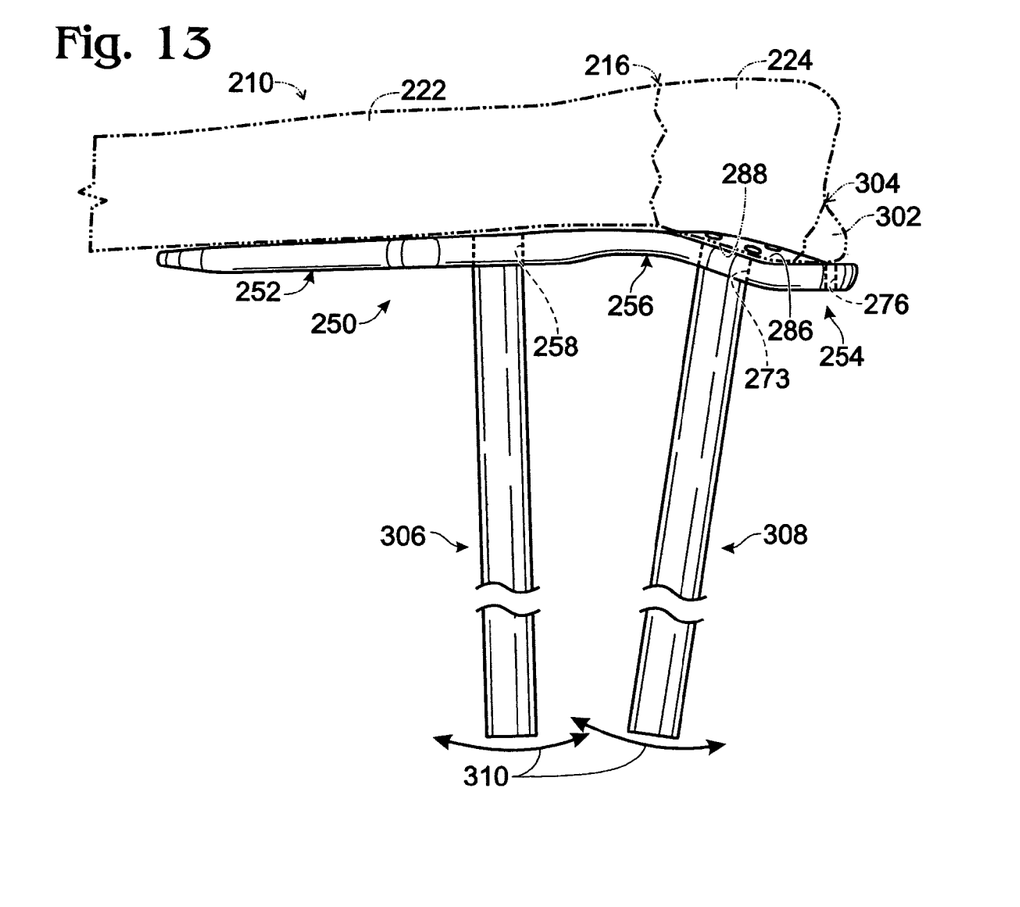
FIG. 13 is a side elevation view of the bone plate of FIG. 12 positioned on a distal portion of a left radius and coupled to tools configured to apply a deforming torque to the bone plate, in accordance with the present teachings.

This example describes deformable bone plates and associated tools for fixing a discontinuity, such as a break or a cut, in a distal portion of the radius; see FIGS. 11–13.

FIG. 11 shows fractured radius 210 fixed with a fifth example of a deformable bone plate 212. Bone plate 212 may be configured to be secured to a distal portion of the radius, such as on volar surface 214, and spanning a discontinuity in the radius, such as fracture 216. Bone plate 212 may include a proximal anchor portion 218 and a distal anchor portion 220 for securing to proximal and distal bone regions 222, 224, respectively. The plate also may include a bridge region 226 connecting the anchor portions. Bridge region may be selectively deformed based on a structural difference from the anchor portions, for example, being narrowed as shown here. Alternatively, or in addition, the bridge region may be selectively deformed by directed application of a deforming torque to the bridge region, such as through tool-engagement sites 228, 230, as described elsewhere in the present teachings. Bone plate 212 may be larger and sturdier than bone plates for phalanx fractures. Accordingly, a larger torque may be necessary to deform the bone plate, and thus handles of the tools may be longer and/or positioned farther from the tool-engagement sites to create a longer lever or moment arm.

FIG. 12 shows a sixth example of a deformable bone plate 250. Bone plate 250 may be configured to be secured to a distal portion of the radius, to fix a discontinuity thereof. Bone plate 250 may be asymmetrical and configured for use on only one side of the body, on the left radius in the present illustration. Bone plate 250 may include a proximal anchor portion 252, a distal anchor portion 254, and a deformable bridge region 256 joining the proximal and distal anchor portions.

Proximal anchor portion 252 may be an axial portion configured to be generally aligned with the long axis of the radius. Proximal anchor portion 252 may define a plurality of openings, 258 to 264, for receiving fasteners, such as bone screws. Proximal opening 264 may be a slot disposed at least substantially parallel to the long axis of proximal anchor portion 252. Each of the openings may be threaded or nonthreaded and may include or lack a counterbore. In some embodiments, one or more of the openings, such as opening 258, may be configured as a transverse slot. One or more of the openings, also or alternatively may be configured to receive a deformation tool, such as a tip of the tool. In the present illustration, opening 258 is threaded and configured to receive the tool so that the tool is disposed in threaded engagement with the bone plate.

At least a subset of the openings may be disposed in a staggered arrangement, such as on opposing sides of a central axis 266 of the plate, to direct bone screws along staggered, nonparallel paths, as described in the following patent application, which is incorporated herein by reference: U.S. Provisional Patent Application Ser. No. 60/512,111, filed Oct. 17, 2003. Accordingly, openings of this subset may define different paths of travel for bone screws based on different orientations of the walls of the openings and/or threads thereof. The perimeter of proximal anchor portion 252 may generally follow the disposition of the openings, to create a wavy or wiggly appearance to the proximal portion when viewed from a position normal to a plane defined by the plate (with the plate's length and width).

Distal anchor portion 254 may be configured to be secured to the widened distal region of the radius. Accordingly, distal anchor portion 254 may be wider than proximal anchor portion 252 and may flare distally, to produce a fan-like shape, so that the plate overall is generally T-shaped. Distal anchor portion 254 may define a plurality of openings 272–274 arrayed in a direction generally transverse to central axis 266 of the proximal anchor portion 252, in one or more rows. Openings 272–274 may be arrayed in one or more linear or arcuate rows, among others.

The distal openings may be threaded, shown at 272 and 273, or nonthreaded, shown at 274, or a combination thereof, as in the present illustration. Each opening may be configured to receive a bone screw or other fastener (such as a pin) at a fixed angle or at a selected angle with a range of angles. The choice between a fixed or variable angle may be defined by how closely the screw or other fastener fits into the opening, and/or whether threaded engagement is used to fix the angle of the screw/fastener. One or more of the openings, also or alternatively may be configured to receive a deformation tool, such as a tip of a handle. In the present illustration, opening 273 is configured to receive the tool.

Distal anchor portion 254 may include one or more additional openings 276 disposed distally of openings 272–274. Opening 276 may be used, for example, to receive a fastener placed into the styloid process of the distal radius, particularly when the styloid process has been fractured.

Distal anchor portion 254 may be contoured to fit on the volar surface of the distal radius. Accordingly, the distal anchor portion 254 may have an inner surface 278 that is transversely convex, and an outer surface 280 that is transversely concave, particularly in a proximal section 282 of distal anchor portion 254. A distal section 284 of distal anchor portion 254 may be configured to be disposed distally of a volar-distal rim of the radius. Accordingly, distal anchor portion 254 may include a transverse contour 286, such as a slight depression, at the junction between proximal and distal sections 282, 284 of the distal anchor portion. Transverse contour 286 may be configured to receive the volar-distal rim 288 of the radius (see FIG. 13). The perimeter of distal anchor portion 254 may be shaped to correspond generally to the outline of the distal radius. For example, the distal-lateral perimeter 290 of the distal anchor portion 254 may be more angular and/or extend farther distally, and the distal-medial perimeter 292 may be more rounded.

Bridge region 256 may include a deformation region 294. The deformation region may be narrowed relative to flanking segments of the plate, as shown here, and/or may differ form the flanking segments in one or more other aspects, as described above in Section II.A and elsewhere in Section III.

FIG. 13 shows bone plate 250 disposed on the volar surface of distal radius 210. Proximal anchor portion 252 may be secured to proximal bone segment 222, and distal anchor portion 254 to distal bone fragment 224. Bridge region 256 may be disposed adjacent a proximal fracture 216 (or cut) of the bone. Distal anchor portion 254 may extend over volar-distal rim 288 of the radius so that styloid process 302 may be secured to distal anchor portion 254 using a fastener placed in opening 276. Accordingly, a styloid fracture 304 may be spanned by distal anchor portion 254. The outer surface of the bone plate may be longitudinally concave, as shown here, to follow the contour of the volar surface of the distal radius.

Tools 306, 308 for deformation of the bone plate may be coupled to openings 258, 273, respectively. The bridge region 256 may be deformed by moving the tools relative to one another, shown at 310.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A method of bone fixation, comprising:
securing anchor portions of a bone plate to respective bone regions disposed on opposing sides of a bone discontinuity; and
deforming the bone plate after the step of securing to change a relative angular disposition of the anchor portions and thus of the respective bone regions to which the anchor portions are secured,
wherein the step of deforming is performed with at least one tool, the method further comprising a step of engaging the bone plate with the at least one tool before the step of deforming,
wherein the step of engaging includes a step of placing a portion of the at least one tool into an opening of the bone plate, and
wherein the step of placing includes a step of rotating the at least one tool into threaded engagement with the bone plate.

2. The method of claim 1, wherein the step of securing includes a step of securing the bone plate to each of at least two bones.

3. The method of claim 1, wherein the step of securing includes a step of placing bone screws through openings of the anchor portions and into the respective bone regions.

4. The method of claim 1, wherein the step of securing includes a step of securing the anchor portions to a radius bone.

5. The method of claim 4, wherein the step of securing includes a step of securing the anchor portions adjacent a volar surface of the radius bone.

6. The method of claim 4, wherein the step of securing the anchor portions to a radius bone includes a step of securing the anchor portions to a distal portion of the radius bone.

7. The method of claim 1, wherein the step of deforming includes a step of twisting the anchor portions relative to one another.

8. The method of claim 1, wherein the step of deforming includes a step of bending the anchor portions relative to one another.

9. The method of claim 1, wherein the bone plate has a bridge region disposed between the anchor portions, and wherein the step of deforming includes a step of selectively deforming the bone plate within the bridge region.

10. The method of claim 1, wherein the step of deforming includes a step of adjusting the relative angular disposition of the bone regions to more closely approximate a natural alignment of the bone regions.

11. The method of claim 1, wherein the step of engaging also includes a step of gripping the bone plate with the at least one tool.

12. A method of bone fixation, comprising:
   securing anchor portions of a unitary bone plate to respective bone regions disposed on opposing sides of a bone discontinuity by placing fasteners through apertures defined by each anchor portion; and
   applying a deforming torque to the bone plate after the step of securing to change a relative angular disposition of the anchor portions and thus of the respective bone regions to which the anchor portions are secured,
   wherein the step of applying a deforming torque is performed with at least one tool, further comprising a step of placing the at least one tool in threaded engagement with the bone plate.

13. The method of claim 12, wherein the step of securing includes a step of placing bone screws through the apertures and into the respective bone regions.

14. The method of claim 12, wherein the step of securing includes a step of securing the anchor portions to a radius bone or a finger bone.

15. The method of claim 12, wherein the bone plate has a bridge region disposed between the anchor portions, and wherein the step of applying a deforming torque includes a step of selectively deforming the bone plate within the bridge region.

16. The method of claim 12, wherein the step of placing the at least one tool includes a step of placing a pair of tools in threaded engagement with spaced apertures of the bone plate, and wherein the step of applying a deforming torque includes a step of selectively deforming the bone plate between the spaced apertures using the pair of tools.

17. A method of bone fixation, comprising:
   securing anchor portions of a unitary bone plate to respective bone regions disposed on opposing sides of a discontinuity in a bone by placing bone screws through apertures defined by the anchor portions;
   placing at least a pair of tools into a pair of openings disposed at spaced positions along the bone plate; and
   applying a deforming torque to the bone plate via the pair of tools after the step of securing to change a relative angular disposition of the anchor portions and thus of the respective regions of the bone to which the anchor portions are secured,
   wherein the step of placing includes a step of placing the pair of tools in threaded engagement with the pair of openings.

18. The method of claim 17, wherein the step of securing includes a step of securing the anchor portions to a distal portion of a radius bone.

* * * * *